(12) United States Patent
Moretti et al.

(10) Patent No.: US 7,378,383 B2
(45) Date of Patent: May 27, 2008

(54) PERFUMING INGREDIENTS OF THE WOODY TYPE

(75) Inventors: Robert Moretti, Geneva (CH); Olivier Etter, Chene-Bourg (CH)

(73) Assignee: Firmenich SA, Geneva (CH)

( * ) Notice: Subject to any disclaimer, the term of this patent is extended or adjusted under 35 U.S.C. 154(b) by 585 days.

(21) Appl. No.: 11/123,759

(22) Filed: May 6, 2005

(65) Prior Publication Data

US 2005/0272632 A1 Dec. 8, 2005

(30) Foreign Application Priority Data

Jun. 8, 2004 (EP) .................... 04102577

(51) Int. Cl.
*A61Q 13/00* (2006.01)
(52) U.S. Cl. ............. 512/15; 512/16; 512/17; 512/19
(58) Field of Classification Search ........... 512/15, 512/16, 17, 19
See application file for complete search history.

(56) References Cited

U.S. PATENT DOCUMENTS 5,114,915 A * 5/1992 Fehr et al. ............ 512/15

OTHER PUBLICATIONS

STIC Search Report dated on Jan. 30, 2008.*
E. Charles Angell et al., "Diels-Alder Reactions of Cycloalkenones. II. Regioselectivity of 2-Cyclohexenones[1]", Journal of Organic Chemistry, vol. 51, No. 26, pp. 5177-5182 (1986).

* cited by examiner

*Primary Examiner*—Eisa B Elhilo
(74) *Attorney, Agent, or Firm*—Winston & Strawn LLP

(57) ABSTRACT

The present invention relates to the use as perfuming ingredient of a decaline derivative of formula

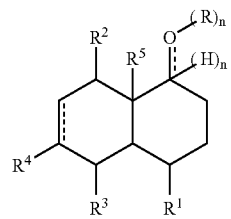

(I)

wherein $R^1$ is a lower alkyl, the $R^2$ to $R^5$ are hydrogen atoms or lower alkyls and at least one dotted line is a double bond, which is a useful perfuming ingredient of the woody or woody-citrus type.

11 Claims, No Drawings

PERFUMING INGREDIENTS OF THE WOODY TYPE

TECHNICAL FIELD

The present invention relates to the field of perfumery. More particularly, it concerns the use as perfuming ingredient of a decaline derivative of formula

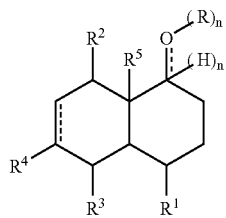
(I)

wherein $R^1$ is a lower alkyl, the $R^2$ to $R^5$ are hydrogen atoms or lower alkyls and at least one dotted line is a double bond.

BACKGROUND

The compounds of formula (I) are generally known from the prior art, where they are described, in general, in the context of chemical synthesis.

However, the prior art documents disclosing said compounds do not report or suggest any organoleptic properties of the compounds of formula (I), or any use of said compound in the field of perfumery.

SUMMARY OF THE INVENTION

The present invention concerns perfuming compositions or perfumed articles comprising a decaline derivative of formula (I) as well as specific compounds of formula (I). Also claimed is a method to impart an odour by using a compound of formula (I).

DETAILED DESCRIPTION OF THE PREFERRED EMBODIMENTS

We have now discovered that a compound of formula

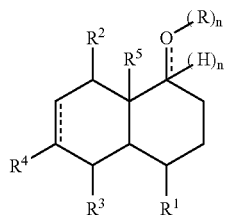
(I)

wherein the dotted lines represent a single or double bond and at least one of said dotted lines represents a double bond; n represents simultaneously 0, in which case the oxygen atom is bounded to the cyclanic carbon atom by a double bond, or 1, in which case the oxygen atom is bounded to the cyclanic carbon atom by a single bond,
R represents a hydrogen atom or a HCO or MeCO group;
$R^1$ represents a linear or branched $C_1$-$C_4$ alkyl or alkenyl group;
$R^2$ represents a hydrogen atom or a methyl or ethyl group;
$R^3$ represents, taken alone, a hydrogen atom or, taken together with $R^2$, a bridging $CH_2$ group;
$R^4$ represents a hydrogen atom or a methyl or ethyl group; and
$R^5$ represents a hydrogen atom or a linear or branched $C_1$-$C_3$ alkyl group;

is a useful perfuming ingredient, which is characterized by an odor of the woody type with optionally citrus notes.

The compound of formula (I) possesses several asymmetric carbon atoms. Therefore, the compound of formula (I) can be in the form of any one of its stereoisomers. Furthermore it is also understood that the invention's compound can be in the form of a mixture of any one of said stereoisomers.

Preferably, substituents $R^1$, $R^2$, $R^3$, $R^4$ and $R^5$ have in total, i.e. all together, 3, 4 or 5 carbon atoms.

According to another embodiment of the invention, the compounds of formula (I) wherein the dotted lines, $R^3$ and n are defined as above;
R represents a hydrogen atom or a MeCO group;
$R^1$ represents a methyl, ethyl or propyl group;
each $R^2$, $R^4$ and $R^5$ represent a hydrogen atom or a methyl group; and
the substituents $R^1$, $R^2$, $R^3$, $R^4$ and $R^5$ have in total, i.e. all together, 3 or 4 carbon atoms;

are particularly suitable of a large number of applications in fine or functional perfumery.

Furthermore, the compounds of formula

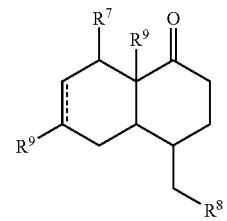
(II)

wherein the dotted lines represent a single or double bond, R represents a hydrogen atom or a MeCO group;
$R^7$ and $R^8$ represent, each, a hydrogen atom or a methyl group;
$R^9$ are both hydrogen atoms or are both methyl groups; and
the substituents $R^7$, $R^8$ and $R^9$ have in total, i.e. all together, 2 or 3 carbon atoms;

or the compounds of formula

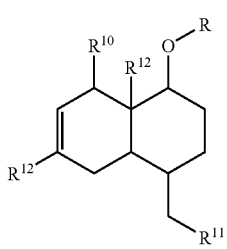
(III)

wherein R represents a hydrogen atom or a MeCO group;
$R^{10}$ and $R^{11}$ represent, each, a hydrogen atom or a methyl group;

one $R^{12}$ is a hydrogen atom and the other is a methyl group; and the substituents $R^{10}$, $R^{11}$ and $R^{12}$ have in total, i.e. all together, 2 or 3 carbon atoms;

are very appreciated by the perfumers for their woody-vetiver/cedar or woody-grapefruit note. The compounds of formula (II) or (III), at the exception of 4,6,8,8a-tetramethyl-3,4,4a,5,8,8a-hexahydro-naphthalenone and 4,6,8a-trimethyl-3,4,4a,5,8,8a-hexahydro-1(2H)-naphthalenone and their isomers, are also new and are a further object of the present invention. The known compounds of formula (II) or (III) have been reported by C. Angell et all in J. Org. Chem. 1986, 51, 5177, wherein they were prepared for a NMR study of geminal di-methyl analogues.

Amongst the compounds responding to the formulae cited above, one may cite in particular, and as non-limiting example, 4,6,8a-trimethyl-3,4,4a,5,8,8a-hexahydro-1(2H)-naphthalenone. This compound has a scent characterized by a woody-cedar and ambery-leather note as well as a jute, patchouli and agarwood connotation. In fact 4,6,8a-trimethyl-3,4,4a,5,8,8a-hexahydro-1(2H)-naphthalenone has an odor which reminds of Vertofix® (methyl cedryl ketone; origin: IFF, USA) but having a greater substantivity and volume than the odor of the latter.

The fragrance and performance of 4,8,8a-trimethyl-1,2,3,4,4a,5,8,8a-octahydro-1-naphthalenyl acetate are very similar to those of the above-cited 4,6,8a-trimethyl-3,4,4a,5,8,8a-hexahydro-1(2H)-naphthalenone, but distinguish themselves by the presence of an additional note of the ozone type.

Another example of invention's compound is perhydro-4-ethyl-8-methyl-1-naphthalenone that has an odor of the woody-vetiver type, with a strong connotation of the vetiveryl acetate, vetiverone type in which the woody, earthy and rooty notes are married in a very natural and elegant manner. It is very rare for a product to possess such a natural vetiver note.

Furthermore, as ketone one may also cite perhydro-8-methyl-4-propyl-1-naphthalenone which has a woody-vetyver note similar to that of perhydro-4-ethyl-8-methyl-1-naphthalenone but possess also a well distinct grapefruit, rhubarbe note.

The scent of 4-ethyl-6,8-dimethyl-1,2,3,4,4a,5,8,8a-octahydro-1-naphthalenol has a quite distinct odor compared to the above-mentioned compounds. The odor of said naphthalenol is characterized by a woody-pin note and a clean, elegant, fresh and powerful citrus note, of the grapefruit type, which reminds of the odor of Nootkatone, a natural ingredient of pink-grapefruit peel scent. Furthermore, 4-ethyl-6,8-dimethyl-1,2,3,4,4a,5,8,8a-octahydro-1-naphthalenol possesses a fragrance having an astonishing substantivity, which is rare for this type of note.

Contrary to the above-mentioned alcohol, the tri-cyclic alcohol 2,6-dimethyltricyclo[6.2.1.0(2,7)]undec-9-en-3-ol possesses a woody odor which is typically of the patchouli and rooty type.

Finally, one may also cite the perhydro-4-ethyl-6,8a-dimethyl-1-naphthalenone and its olefinic analogue 4-ethyl-6,8a-dimethyl-3,4,4a,5,8,8a-hexahydro-1(2H)-naphthalenone. Both compounds have a scent similar to that of perhydro-4-ethyl-8-methyl-1-naphthalenone, but are a bit less strong and have also a grapefruit note, which is stronger for the perhydro-4-ethyl-6,8a-dimethyl-1-naphthalenone.

As mentioned above, the invention concerns also the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing the compound (I) and which can be advantageously employed in the perfumery industry as active ingredients.

Said compositions, which are in fact perfuming compositions that can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for example, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the organoleptic effect desired. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Its is also understood here that any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I) as defined above; and
ii) a consumer product base, is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 25% by weight, or even more, of the compounds of the invention based on the weight of the composition into which they are incorporated. Concentrations lower than these, such as in the order of 1% to 10% by weight, can be used when these compounds are incorporated into perfumed articles.

The use and article comprising an invention's compound selected from the group consisting of the 4,6,8a-trimethyl-3,4,4a,5,8,8a-hexahydro-1(2H)-naphthalenone, 4-ethyl-6,8-dimethyl-1,2,3,4,4a,5,8,8a-octahydro-1-naphthalenol, perhydro-4-ethyl-8-methyl-1-naphthalenone and perhydro-8-methyl-4-propyl-1-naphthalenone are a preferred embodiment of the invention. Three of said compounds are also new and are also an object of the present invention.

The invention's compounds can be prepared by a process involving a Lewis acidic catalyzed Diels-Alder reaction between a diene of formula (IV) and a dienophyle of formula (V),

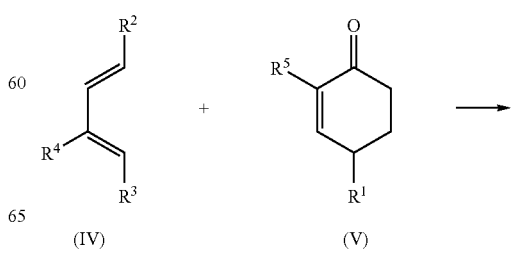

(IV)　　　　　　(V)

-continued

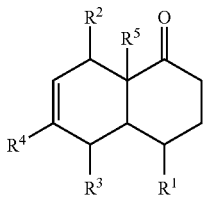

wherein the symbols have the meaning indicated above, and then optionally a reduction of the carbonyl or of the carbon-carbon double bond. Specific examples are given further below.

EXAMPLES

The following examples are further illustrative of the present invention embodiments. In the following examples, the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Synthesis of Compounds of Formula (I)

The 4-ethyl-cyclohex-2-enone is a known compound (see Duhamel et al in Tetrahedron, 1986, 42, 4777) as well as 2,4-dimethyl-cyclohex-2-enone (see Blanc et al in Helv. Chim. Acta, 1964, 725).

1) Synthesis of the Starting Cyclohexenones

General Procedure for the First Step

In an appropriate vessel were introduced the aldehyde, the vinyl-ketone, diethylamine, and toluene and the mixture was heated 20 hours at 90° C. under good stirring. Afterwards, the temperature was dropped to 25° C. and the reaction mixture was hydrolyzed with 5% aqueous HCl and extracted twice with $Et_2O$. The organic layer was then washed with a saturated $NaHCO_3$ aqueous solution, water, brine and then dried over $Na_2SO_4$. Evaporation of the solvents and distillation provided the end product.

a) 2-Ethyl-5-oxoheptanal

Starting materials and quantities: Butyraldehyde (400 mmol)
Ethylvinylketone (600 mmol)
Diethylamine (80 mmol)
Toluene (200 ml)
Was obtained with a yield of 80%.
B.p.=85° C. at 1.1 mbar MS: 156 (M+, 2); 138 (6); 128 (12); 127 (14); 109 (10); 99 (30); 85 (28); 81 (41); 72 (60); 57 (100); 55 (40). $^1H$-NMR: 0.95 (t, J=7, 3H); 1.05 (t, J=7, 3H); 1.40-1.92 (m, 4H); 2.12-2.25 (m, 1H); 2.32-2.52 (m, 4H), 9.57 (d, J=2.4 Hz, 1H).

b) 5-Oxo-2-propylheptanal

Starting materials and quantities: Valeraldehyde (630 mmol)
Ethylvinylketone (950 mmol)
Diethylamine (130 mmol)
Toluene (400 ml)
Was obtained with a yield of 97%.
B.p.=93° C. at 1.7 mbar MS: 170 (M+, 3); 152 (5); 141 (21); 123 (18); 113 (33); 99 (11); 95 (45); 85 (22); 81 (13); 72 (72); 57 (100); 55 (37) $^1H$-NMR: 0.92 (t, J=7, 3H); 1.04 (d, J=7, 3H); 1.30-1.47 (m, 3H); 1.60-1.93 (m, 3H); 2.20-2.32 (m, 1H); 2.35-2.52 (m, 4H); 9.54 (d, J=2.4 Hz, 1H).

c) 5-Oxo-2-propylhexanal

Starting materials and quantities: Valeraldehyde (0.8 mol)
Methylvinylketone (1.2 mol)
Diethylamine (0.16 mol)
Toluene (500 ml)
Was obtained with a yield of 93%.
B.p.=94° C. at 1.1 mbar. MS: 156 (M+; 1); 138 (5); 127 (15); 114 (9); 109 (10); 99 (9); 95 (13); 86 (20); 81 (12); 71 (18); 58 (100); 43 (93). $^1H$-NMR: 0.92 (t, J=7 Hz, 3H); 1.30-1.48 (m, 3H); 1.60-1.95 (m, 3H); 2.13 (s, 3H); 2.22-2.32 (m, 1H); 2.38-2.55 (m, 2H); 9.55 (d, J=2.4 Hz, 1H).

General Procedure for the Second Step

In an appropriate vessel were introduced aqueous KOH and tetramethylammonium hydroxide in THF. Then the compound obtained in the first step, in $Et_2O$, was added dropwise and the mixture stirred 2 hours, at room temperature. When the reaction ended, the mixture was hydrolyzed with 5% aqueous HCl and extracted twice with $Et_2O$. The organic layer was then washed with a saturated $NaHCO_3$ aqueous solution, water, brine and then dried over $Na_2SO_4$. Evaporation of the solvents and distillation provided the end product.

a) 4-Ethyl-2-methyl-2-cyclohexen-1-one

Starting materials and quantities:
the compound obtained in the first step (a) (440 mmol)
Teramethylammonium hydroxide (37 mmol)
KOH (90 mmol), in 100 ml of water
THF (100 ml)
$Et_2O$ (100 ml)
Was obtained with a yield of 93%.
B.p.=89° C. at 3.0 mbar MS: 138 (M+, 94); 123 (8); 109 (20); 96 (86); 95 (60); 81 (100); 79 (30); 69 (19); 67 (29) $^1H$-NMR: 1.01 (t, J=7, 3H); 1.38-1.60 (m, 3H); 1.75 (broad s, 3H); 2.02-2.12 (m, 1H); 2.25-2.38 (m, 2H); 2.50 (m, 1H); 6.62 (m, 1H).

b) 2-Methyl-4-propyl-2-cyclohexen-1-one

Starting materials and quantities:
the compound obtained in the first step (b) (610 mmol)
Teramethylammonium hydroxide (55 mmol)
KOH (180 mmol), in 200 ml of water
THF (200 ml)
$Et_2O$ (200 ml)
Was obtained with a yield of 86%.
B.p.=93° C. at 2.5 mbar MS: 152 (M+, 76); 123 (10); 110 (41); 109 (23); 95 (100); 82 (85); 81 (60); 79 (25); 69 (19); 67 (25). $^1H$-NMR: 0.93 (t, J=7, 3H); 1.30-1.50 (m, 4H); 1.55-1.70 (m, 1H); 1.75 (broad s, 3H); 2.02-2.14 (m, 1H); 2.27-2.45 (m, 2H); 2.50 (m, 1H); 6.60 (m, 1H).

c) 3-Propyl-2-cyclohexen-1-one

Starting materials and quantities:
the compound obtained in the first step (c) (0.764 mol)
Tetramethylammonium hydroxide pentahydrate (0.066 mol)
Potassium hydroxide (10 g, 0.15 mol) in water (200 ml)
THF (200 ml)
Diethylether (200 ml)
Was obtained with a yield of 82%.
B.p.=84° C. at 2.5 mbar. MS: 138 (M+, 52); 110 (28); 96 (43); 81 (100); 53 (17); 41 (17). $^1H$-NMR 0.95 (t, J=7, 3H); 1.20-1.73 (5H); 2.05-2.20 (m, 1H); 2.28-2.53 (m, 3H); 5.96 (dd, $J_1$=10.3 Hz, $J_2$=2.4 Hz, 1H); 6.87 (m, 1H).

2) Synthesis of the Compounds of Formula (I)

I) General Procedure for the Diels-Alder Coupling

In a 500 ml reactor were introduced the AlEtCl$_2$, or the AlCl$_3$, 0.1 g of BHT and toluene, or CH$_2$Cl$_2$. Then, under vigorous stirring, was added the appropriate cyclohexenone dropwise, so as to maintain the temperature below 30° C. Afterward, was added the diene dropwise and when the reaction ended the reaction mixture was hydrolyzed with 5% aqueous HCl, extracted twice with Et$_2$O. The organic layer was then washed with a saturated NaHCO$_3$ aqueous solution, water, brine and then dried over Na$_2$SO$_4$. Evaporation of the solvents, chromatography (SiO$_2$, elution heptane/AcOEt 98:2) and distillation provided the end product.

a) 4,6,8a-Trimethyl-3,4,4a,5,8,8a-hexahydro-1(2H)-naphthalenone

Starting materials and quantities: 2,4-Dimethyl-2-cyclohexen-1-one (320 mmol)

AlCl$_3$ (80 mmol)
Isoprene (4.8 mol)
Toluene (500 ml)

Was obtained with a yield of 83%, in the form of a mixture of isomers (88/4/9).

B.p.=78° C. at 0.023 mbar MS (major isomer): 192 (M+, 14); 177 (32); 159 (44); 149 (100); 132 (36); 119 (21); 93 (33); 91 (33); 77 (16). $^1$H-NMR: 0.94 (d, J=7, 3H); 1.10 (s, 3H); 1.25-1.43 (m, 3H); 1.58-2.80 (m, 7H); 1.67 (broad s, 3H); 5.25-5.35 (m, 1H).

b) 4-Ethyl-6,8a-dimethyl-3,4,4a,5,8,8a-hexahydro-1 (2H)-naphthalenone

Starting materials and quantities: 4-Ethyl-2-methyl-2-cyclohexen-1-one (109 mmol)

AlCl$_3$ (27 mmol)
Isoprene (218 mmol)
Toluene (150 ml)

Was obtained with a yield of 68%, in the form of a mixture of isomers (93/2/5).

B.p.=85° C. at 0.004 mbar MS (major isomer): 206 (M+, 11); 191 (25); 173 (12); 163 (100); 159 (39); 132 (19); 119 (14); 107 (23); 93 (24); 91 (24). $^1$H-NMR: 0.87 (t, J=7, 3H); 1.08 (s, 3H); 1.13-1.70 (m, 6H); 1.18 (broad s, 3H); 1.97-2.07 (m, 3H); 2.30 (m, 1H); 2.40 (m, 1H); 2.70 (m, 1H); 5.32 (m, 1H).

c) 4-Ethyl-8-methyl-3,4,4a,5,8,8a-hexahydro-1(2H)-naphthalenone

Starting materials and quantities: 4-Ethyl-2-cyclohexen-1-one (144 mmol)

EtAlCl$_2$ (60 mmol)
Piperylene (288 mmol)
CH$_2$Cl$_2$ (150 ml)

Was obtained with a yield of 60%, in the form of a mixture of isomers (20/7/81/90).

B.p.=85° C. at 0.042 mbar MS (major isomer): 192 (M+, 59); 177 (17); 163 (21); 145 (100); 133 (34); 121 (49); 93 (79); 79 (48); 77 (42). $^1$H-NMR: 0.85-1.03 (m, 3H); 1.15-1.55 (m, 5H); 1.60-2.50 (m, 9H); 2.72-2.92 (m, 1H); 5.42-5.60 (m, 2H).

d) 4-Ethyl-6,8-dimethyl-3,4,4a,5,8,8a-hexahydro-1(2H)-naphthalenone

Starting materials and quantities: 4-Ethyl-2-cyclohexen-1-one (80 mmol)

EtAlCl$_2$ (40 mmol)
Methylpentadiene (160 mmol)
CH$_2$Cl$_2$ (200 ml)

Was obtained with a yield of 68%, in the form of a mixture of isomers (19/78/3).

B.p.=105° C. at 0.031 mbar MS (major isomer): 206 (M+, 88); 191 (63); 177 (15); 173 (17); 159 (91); 147 (51); 135 (73); 119 (34); 107 (100); 91 (60). $^1$H-NMR: 0.85-1.05 (m, 6H); 1.20 (m, 3H); 1.40-2.85 (m, 12H); 5.14-5.43 (m, 1H). Odor: woody, rhubarb, balsamic and grapefruit with some bottom notes of the earthy, humid or marine type e) (1RS,2RS,6RS,7SR,8SR)-2,6-dimethyltricyclo[6.2.1.0 (2,7)]undec-9-en-3-one Starting materials and quantities: 2,4-Dimethyl-2-cyclohexen-1-one (91 mmol)

EtAlCl$_2$ (45.5 mmol)
Cyclopentadiene (182 mmol)
CH$_2$Cl$_2$ (100 ml)

Was obtained with a yield of 61%, in the form of a mixture of isomers (14/79/2/4).

B.p.=88° C. at 0.024 mbar MS (major isomer): 125 (100); 107 (8); 91 (11); 66 (96). $^1$H-NMR: 0.98-1.10 (m, 6H); 1.12-2.00 (m, 5H); 2.20-3.20 (m, 5H); 5.92-6.40 (m, 2H). Odor: woody, camphoraceous and champhene f) 4,8,8a-Trimethyl-3,4,4a,5,8,8a-hexahydro-1(2H)-naphthalenone Starting materials and quantities: 2,4-Dimethyl-2-cyclohexen-1-one (60 mmol)

EtAlCl$_2$ (60 mmol)
Piperylene (450 mmol)
CH$_2$Cl$_2$ (100 ml)

Was obtained with a yield of 70%, in the form of a mixture of isomers (58/42).

B.p.=82° C. at 0.023 mbar MS (major isomer): 192 (M+, 20); 177 (10); 149 (21); 135 (11); 125 (100); 107 (33); 93 (19); 91 (22); 68 (49). MS (minor isomer): 192 (86); 177 (32); 149 (33); 135 (37); 125 (92); 107 (100); 93 (46); 91 (51); 68 (60). $^1$H-NMR: 0.75-1.05 (m, 6H); 1.18-1.48 (m, 5H); 1.65-2.80 (m, 7H); 5.35-5.62 (m, 2H). Odor: woody-camphor and eucalyptus g) 6,8a-Dimethyl-4-propyl-3,4,4a,5,8,8a-hexahydro-1 (2H)-naphthalenone Starting materials and quantities: 4-Propyl-2-methyl-2-cyclohexen-1-one (109 mmol)

AlCl$_3$ (27 mmol)
Isoprene (218 mmol)
Toluene (150 ml)

Was obtained with a yield of 37%, in the form of a mixture of isomers (92/4/4).

B.p.=81° C. at 0.045 mbar MS (major isomer): 220 (M+, 15); 205 (29); 202 (14); 177 (100); 159 (48); 135 (37); 132 (36); 119 (18); 107 (27); 93 (30); 91 (31). $^1$H-NMR: 0.92 (t, J=7, 3H); 1.08 (s, 3H); 1.10-1.70 (m, 9H); 1.68 (broad s, 3H); 2.05 (m, 2H); 2.30 (m, 1H); 2.40 (m, 1H); 2.70 (m, 1H); 5.32 (m, 1H). Odor: woody-vetiver and grapefruit-nootkatone h) 4,6,8,8a-Tetramethyl-3,4,4a,5,8,8a-hexahydro-1(2H)-naphthalenone Starting materials and quantities: 2,4-Dimethyl-2-cyclohexen-1-one (58 mmol)

EtAlCl$_2$ (29 mmol)
Methylpentadiene (117 mmol)
CH$_2$Cl$_2$ (150 ml)

Was obtained with a yield of 90%, in the form of a mixture of isomers (89/11).

B.p.=85° C. at 0.065 mbar MS (major isomer): 206 (M+, 16); 191 (8); 177 (10); 73 (8); 163 (23); 125 (43); 121 (22); 107 (19); 105 (13); 91 (16); 82 (100); 67 (36). $^1$H-NMR: 0.70-1.20 (m 9H); 1.30-2.80 (m, 12H); 5.05-5.40 (m, 1H). Odor: woody, naphthalene and grapefruit i) 8-Methyl-4-propyl-3,4,4A,5,8,8A-hexahydro-1(2H)-naphthalenone Starting materials and quantities: 4-Propyl-2-cyclohexen-1-one (0.1 mol)

Ethyl aluminium dichloride (20 ml, 0.02 mol)

Piperylene (0.2 mol)
CH$_2$Cl$_2$ (150 ml).
Was obtained with a yield of 52%, in the form of a mixture of isomers (Oct. 3, 1945/42).
B.p.=80° C. at 0.021 mbar MS (major isomer): 206 (M+, 49); 191 (14); 177 (7); 163 (15); 145 (100); 136 (20); 121 (59); 105 (47); 93 (81); 79 (51); 77 (42); 67 (23); 55 (34); 41 (36). $^1$H-NMR: 0.88-1.02 (m, 3H); 1.20 (m, 3H); 1.25-2.50 (m, 13H); 2.72-2.92 (m, 1H); 5.45-5.60 (m, 2H).

II) General Procedure for the Reduction of the Ketone Into the Alcohol

In a 100 ml flask, maintained under Ar atmosphere, were introduced 2 molar equivalents, with respect of the ketone, of LiAlH$_4$ in l'Et$_2$O. Then the appropriate naphthalenone was added dropwise, so as to maintain the reflux. After completion of the reaction the mixture was stirred for 30 minutes at reflux. Afterwards the reaction mixture was hydrolyzed with a stoechiometric amount of aqueous NaOH and the organic layer was dried over Na$_2$SO$_4$. Evaporation of the solvents and distillation provided the end product.

a) 4,8,8a-Trimethyl-1,2,3,4,4a,5,8,8a-octahydro-1-naphthalenol

Starting materials and quantities: Naphthalenone obtained under I.f) (78 mmol)
Et$_2$O (150 ml)
Was obtained with a yield of 79%, in the form of a mixture of isomers (59/34/7).
B.p.=72° C. at 0.002 mbar MS (major isomer): 194 (M+, 2); 176 (45); 161 (34); 147 (11); 135 (18); 133 (13); 125 (39); 119 (100); 109 (91); 93 (49); 91 (41). MS (minor isomer): 194 (M+, 0.2); 176 (26); 161 (21); 119 (100); 107 (19); 105 (38); 93 (24); 91 (23). $^1$H-NMR: 0.78-1.30 (m, 10H); 1.55-2.65 (m, 9H); 3.30-3.90 (m, 1H); 5.22-5.90 (m, 2H). Odor: woody, patchouli and earthy b) 2,6-Dimethyltricyclo[6.2.1.0(2,7)]undec-9-en-3-ol Starting materials and quantities: Naphthalenone obtained under I.e) (21 mmol)
Et$_2$O (400 ml)
Was obtained with a yield of 89%, in the form of a mixture of isomers (18/66/10/4/2).
B.p.=81° C. at 0.008 mbar MS (major isomer): 192 (M+, 0.1); 125 (95); 111 (47); 109 (70); 93 (27); 91 (23); 84 (38); 82 (28); 66 (100). $^1$H-NMR: 0.55-0.95 (m, 6H); 0.95-1.30 (m, 3H); 1.35-2.25 (m, 6H); 2.45-2.90 (m, 2H); 3.65-3.95 (m, 1H); 6.02-6.45 (m, 2H).

c) 4,6,8,8a-Tetramethyl-1,2,3,4,4a,5,8,8a-octahydro-1-naphthalenol

Starting materials and quantities: Naphthalenone obtained under I.h) (36 mmol)
Et$_2$O (50 ml)
Was obtained with a yield of 98%, in the form of a mixture of isomers (25/75).
B.p.=89° C. at 0.039 mbar MS (major isomer): 208 (M+, 4); 190 (39); 175 (36); 133 (88); 119 (41); 107 (39); 91 (30); 82 (100); 67 (38). $^1$H-NMR: 0.75-1.25 (m, 10H); 1.35-2.15 (m, 12H); 3.30-3.55 (m, 1H); 4.95-5.35 (m, 1H). Odor: woody-cedar with bottom notes of the dry pine forest type d) 4-Ethyl-6,8-dimethyl-1,2,3,4,4a,5,8,8a-octahydro-1-naphthalenol Starting materials and quantities: Naphthalenone obtained under I.d) (73 mmol)
Et$_2$O (150 ml)
Was obtained with a yield of 89%, in the form of a mixture of isomers (Mar. 10, 1962/5/11/5/3).
B.p.=89° C. at 0.030 mbar MS (major isomer): 208 (M+, 5); 190 (41); 175 (23); 161 (40); 147 (10); 133 (19); 119 (100); 105 (81); 91 (28). $^1$H-NMR: 0.80-1.10 (m, 6H); 1.15-1.70 (m, 11H); 1.75-2.50 (m, 5H); 3.70-4.10 (m, 1H); 5-05-5.50 (m, 1H)

III) General Procedure for the Hydrogenation of the Naphthalenone Into the Perhydro Naphthalenone In a 100 ml flask were introduced the appropriate naphthalenone, ethyl acetate and 10% w/w, relative to the naphthalenone, of Pd/C$_5$%. The mixture was thus stirred under H$_2$, at a room temperature, until consumption of the theoretical amount of hydrogen. Afterwards, the reaction mixture was filtered over Nylon 6/6. Evaporation of the solvents and distillation provided the end product.

a) Perhydro-4-ethyl-8-methyl-1-naphthalenone

Starting materials and quantities: Naphthalenone obtained under I.c) (52 mmol)
Ethyl acetate (100 ml)
H$_2$ (1.16 l)
Was obtained with a yield of 95%, in the form of a mixture of isomers (35/51/1/12/1).
B.p.=87° C. at 0.050 mbar MS (major isomer): 194 (M+, 28); 165 (30); 151 (14); 138 (14); 125 (100); 110 (11); 95 (30). MS (minor isomer): 194 (M+, 69); 179 (21); 165 (26); 151 (48); 138 (51); 125 (100); 123 (52); 110 (35); 95 (66). $^1$H-NMR: 0.78-1.00 (m, 5H); 110 (m, 3H); 110-2.65 (m, 14H).

b) Perhydro-4-ethyl-6,8a-dimethyl-1-naphthalenone

Starting materials and quantities: Naphthalenone obtained under I.b) (29 mmol)
Ethyl acetate (60 ml)
H$_2$ (650 ml)
Was obtained with a yield of 95%, in the form of a mixture of isomers (6/1/37/2/48/6).
B.p.=95° C. at 0.050 mbar MS (major isomer): 208 (M+, 9); 193 (44); 139 (100); 109 (26); 95 (19); 81 (17). MS (minor isomer): 208 (M+, 2); 139 (100); 109 (17); 95 (12); 81 (12). $^1$H-NMR: 0.80-1.00 (m, 7H); 1.15-1.25 (m, 5H); 1.25-1.75 (m, 8H); 1.85-2.08 (m 2H); 2.15-2.35 (m, 1H); 2.48-2.70 (m, 1H).

c) Perhydro-8-methyl-4-propyl-1-naphthalenone

Starting materials and quantities: Naphthalenone obtained under I.i) (0.058 mol)
Ethyl acetate (120 ml)
H$_2$ (1.3 l)
Was obtained with a yield of 96%, in the form of a mixture of isomers (17/70/5/6/2).
B.p.=85° C. at 0.016 mbar. MS (major isomer): 208 (M+, 50); 190 (5); 179 (40); 165 (21); 139 (100); 123 (30); 110 (97); 95 (55); 81 (29); 67 (23); 55 (33); 41 (23). $^1$H-NMR: 0.85-1.00 (m, 6H); 1.10-2.70 (m, 18H).

IV) General Procedure for the Esterification of the Alcohol

In a 250 ml flask were introduced the appropriate alcohol, CH$_2$Cl$_2$, dimethylamminopyridine, pyridine and the appropriate carboxylic anhydride. The mixture was thus stirred 24 hours at room temperature. When the reaction has finished the reaction mixture was hydrolyzed with 5% aqueous HCl, extracted twice with Et$_2$O. The organic layer was then washed an aqueous solution of CuSO$_4$, a saturated NaHCO$_3$ aqueous solution, water, brine and then dried over Na$_2$SO$_4$. Evaporation of the solvents provided the end product.

a) 4,8,8a-Trimethyl-1,2,3,4,4a,5,8,8a-octahydro-1-naphthalenyl acetate

Starting materials and quantities: Alcohol obtained under II.a) (46 mmol)
CH$_2$Cl$_2$ (100 ml)
Acetic anhydride (69 mmol)
Dimethylamminopyridine (4.6 mmol)
Pyridine (78 mmol)
Was obtained with a yield of 83%, in the form of a mixture of isomers (26/60/33/11).
B.p.=69° C. at 0.008 mbar MS (major isomer): 236 (M+, 0.1); 194 (2); 176 (57); 161 (37); 147 (15); 133 (17); 119

(75); 108 (100); 93 (69). $^1$H-NMR: 0.78-1.30 (m, 11H); 1.35-2.35 (m, 10H); 4.57-4.97 (m, 1H); 5.35-5.90 (m, 2H).

b) 4,6,8,8a-Tetramethyl-1,2,3,4,4a,5,8,8a-octahydro-1-naphthalenyl formate

Starting materials and quantities: Alcohol obtained under II.c) (3.8 mmol)
CH$_2$Cl$_2$ (20 ml)
Acetic anhydride (11.5 mmol) and formic acid
(13.8 mmol) heated 2 hours at 55° C.
Dimethylamminopyridine (not used)
Pyridine (not used).

Was obtained with a yield of 98%, in the form of a mixture of isomers (7/19/74).

B.p.=74° C. at 0.008 mbar MS (major isomer): 236 (M+, 0.2); 190 (30); 175 (25); 133 (52); 121 (19); 119 (26); 107 (28); 105 (15); 82 (100) $^1$H-NMR: 0.80 (m, 3H); 0.85-1.30 (m, 8H); 1.40-2.20 (m, 10H); 4.70-4.88 (m, 1H); 4.96-5.30 (m, 1H); 7-97-8.17 (m, 1H). Odor: woody, ambery and vetiveryl acetate Example 2

Preparation of a Perfuming Composition

An eau de toilette for man, of the citrus type, was prepared by admixing the following ingredients:

| Ingredient | Parts by weight |
| --- | --- |
| Geranyl acetate | 10 |
| Linalyl acetate | 420 |
| 10%* Raspberry ketone | 20 |
| Bergamote essential oil | 200 |
| Citral | 30 |
| Lemon essential oil | 500 |
| 50%** Galaxolide ®$^{1)}$ | 100 |
| 10%* Galbanum essential oil | 90 |
| Clove essential oil | 90 |
| Lavander essential oil | 200 |
| Linalool | 70 |
| Lyral ®$^{2)}$ | 340 |
| Sweet marjoram essential oil | 120 |
| Mousse Chêne | 50 |
| Nutmeg essential oil | 160 |
| 3-(Iso-camphyl-5)-cyclohexanol | 200 |
| Ylang Extra | 100 |
| | 2700 |

*in dipropyleneglycol
**in isopropyl myristate
$^{1)}$1,3,4,6,7,8-hexahydro-4,6,6,7,8,8-hexamethyl-cyclopenta-g-2-benzopyrane; origin: International Flavors & Fragrances, USA
$^{2)}$4/3-(4-hydroxy-4-methylpentyl)-3-cyclohexene-1-carbaldehyde; origin: International Flavors & Fragrances, USA The addition of 800 parts by weight of 4,6,8a-trimethyl-3,4,4a,5,8,8a-hexahydro-1(2H)-naphthalenone to the above-described eau de toilette imparted to the fragrance of the latter a remarkably natural and strong connotation of the woody, cedar, Vertofix®, cedryl acetate, which was very warm and had a lot of volume.

When instead of the above mentioned compound was added the same amount of 4,8,8a-trimethyl-1,2,3,4,4a,5,8,8a-octahydro-1-naphthalenyl acetate the effect obtained was quite similar although slightly less round.

The effect obtained by the addition of 800 parts by weight of perhydro-4-ethyl-8-methyl-1-naphthalenone to the above-described eau de toilette was quite different from the one described for the two compounds mentioned above. The new fragrance thus obtained had now a scent much more in the direction of vetiver, a bit watery and very pleasant and noble.

Also the effect obtained by the addition of 800 parts by weight of 4-ethyl-6,8-dimethyl-1,2,3,4,4a,5,8,8a-octahydro-1-naphthalenol to the above-described fine perfumery composition was very different from the one described for the other compounds mentioned above. The scent became almost of the grapefruit type with a woody bottom note. The grapefruit note was devoid of the classical grapefruit-sulfury note and was reminiscent of nootkatone.

Example 3

Preparation of a Perfuming Composition

A perfuming composition of the citrus type, for a powder detergent, was prepared by admixing the following ingredients:

| Ingredient | Parts by weight |
| --- | --- |
| 1,1-Dimethyl-2-phenylethyl acetate | 20 |
| Citronellyl acetate | 20 |
| Terpenyl acetate | 300 |
| Isobornyl acetate | 20 |
| 10%* Fenchylic alcool | 20 |
| Aldehyde C 12 | 20 |
| 10%* 4-Ethyl-benzaldehyde | 10 |
| Aldehyde MNA | 10 |
| Methyl Anthranilate | 60 |
| Benzylacetone | 20 |
| Borneol | 10 |
| Cashmeran ®$^{1)}$ | 100 |
| Cetalox ®$^{2)}$ | 100 |
| Citronellol | 810 |
| 10%* Coumarine | 40 |
| (−)-(1'R,E)-2-Ethyl-4-(2',2',3'-trimethyl-3'-cyclopenten-1'-yl)-2-buten-1-ol$^{3)}$ | 20 |
| Dihydromyrcenol | 2000 |
| Geranyl Nitrile | 30 |
| Hédione ®$^{4)}$ | 100 |
| Heliotropine | 30 |
| Ionone alpha | 10 |
| Iralia ®$^{5)}$ Total | 20 |
| Lavandin Grosso | 50 |
| Mayol ®$^{6)}$ | 30 |
| 10%* Crystalmoss | 20 |
| Neobutenone ®$^{7)}$ | 20 |
| Nonalactone gamma | 10 |
| Rose oxide | 10 |
| Phenylhexanol | 250 |
| Verdyl propionate | 380 |
| Isobornyl propionate | 300 |
| 10%* Romascone ®$^{8)}$ | 20 |
| Terpineol | 40 |
| Linalool | 70 |
| Undecavertol ®$^{9)}$ | 10 |
| Verdox ®$^{10)}$ | 1500 |
| Yara Yara | 20 |
| | 6500 |

*in dipropyleneglycol
$^{1)}$1,2,3,5,6,7-hexahydro-1,1,2,3,3-pentamethyl-4-indenone; origin: International Flavors & Fragrances, USA
$^{2)}$dodecahydro-3a,6,6,9a-tetramethyl-naphtho[2,1-b]furan; origin: Firmenich SA, Geneva, Switzerland
$^{3)}$origin: Firmenich SA, Geneva, Switzerland
$^{4)}$methyl dihydrojasmonate; origin: Firmenich SA, Geneva, Switzerland
$^{5)}$methyl ionone; origin: Firmenich SA, Geneva, Switzerland
$^{6)}$cis-7-P-menthanol; origin: Firmenich SA, Geneva, Switzerland
$^{7)}$1-(5,5-dimethyl-1-cyclohexen-1-yl)-4-penten-1-one; origin: Firmenich SA, Geneva, Switzerland
$^{8)}$methyl 2,2-dimethyl-6-methylene-1-cyclohexanecarboxylate; origin: Firmenich SA, Geneva, Switzerland
$^{9)}$4-methyl-3-decen-5-ol; origin: Givaudan-Roure, Vernier, Switzerland
$^{10)}$2-tert-butyl-1-cyclohexyl acetate; origin: International Flavors & Fragrances, USA The addition of 1300 parts by weight of 4,6,8a-trimethyl-3,4,4a,5,8,8a-hexahydro-1(2H)-naphthalenone or 4,8,8a-trimethyl-1,2,3,4,4a,5,8,8a-octahydro-1-naphthalenyl acetate to the above-described functional composition imparted a very elegant, as well as particularly persistent, woody-cedar note. The note imparted by 4,6,8a-trimethyl-3,4,4a,5,8,8a-hexahydro-1(2H)-naphthalenone was more elegant and warm than the one imparted by 4,8,8a-trimethyl-1,2,3,4,4a,5,8,8a-octahydro-1-naphthalenyl acetate. Furthermore, the effect imparted by the two invention's compounds was judged by the expert perfumers as being more elegant and performing, in application, than the one which was obtained by the addition of the same amount of Vertofix® to the above-mentioned functional composition. The addition of the same amount of perhydro-4-ethyl-8-methyl-1-naphthalenone to the above-described functional composition imparted a very nice vetiver tonality to the new composition, while the addition of 4-ethyl-6,8-dimethyl-1,2,3,4,4a,5,8,8a-octahydro-1-naphthalenol imparted a fresh and natural citrus connotation, of the pink grapefruit type. The freshness imparted by 4-ethyl-6,8-dimethyl-1,2,3,4,4a,5,8,8a-octahydro-1-naphthalenol was also present on the dry linen, resulting thus in an exceptional performance for a compound having such fragrance notes.

What is claimed is:

1. A perfuming composition comprising
    i) as perfuming ingredient, at least one compound of formula

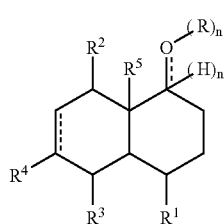

(I)

wherein the dotted lines represent a single or double bond and at least one of said dotted lines represents a double bond;
n represents simultaneously 0, in which case the oxygen atom is bounded to the cyclanic carbon atom by a double bond, or 1, in which case the oxygen atom is bounded to the cyclanic carbon atom by a single bond,
R represents a hydrogen atom or a HCO or MeCO group;
$R^1$ represents a linear or branched $C_1$-$C_4$ alkyl or alkenyl group;
$R^2$ represents a hydrogen atom or a methyl or ethyl group;
$R^3$ represents, taken alone, a hydrogen atom or, taken together with $R^2$, a bridging $CH_2$ group;
$R^4$ represents a hydrogen atom or a methyl or ethyl group; and
$R^5$ represents a hydrogen atom or a linear or branched $C_1$-$C_3$ alkyl group;
in the form of any one of its stereoisomers or of a mixture thereof;
    ii) at least one ingredient selected from the group consisting of a perfumery carrier and a perfumery base; and
    iii) optionally at least one perfumery adjuvant.

2. A perfuming composition according to claim 1, wherein in formula (I) the dotted lines, $R^3$ and n are as defined in claim 1;
R represents a hydrogen atom or a MeCO group;
$R^1$ represents a methyl, ethyl or propyl group;

each $R^2$, $R^4$ and $R^5$ represent a hydrogen atom or a methyl group; and
the substituents $R^1$, $R^2$, $R^3$, $R^4$ and $R^5$ have in total 3 or 4 carbon atoms.

3. A perfuming composition according to claim 1, wherein the perfuming ingredient is a compounds of formula

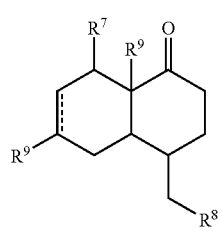

(II)

wherein the dotted lines represent a single or double bond;
$R^7$ and $R^8$ represent, each, a hydrogen atom or a methyl group;
$R^9$ are both hydrogen atoms or are both methyl groups; and
the substituents $R^7$, $R^8$ and $R^9$ have in total 2 or 3 carbon atoms; in the form of any one of its stereoisomers or of a mixture thereof;
or a compounds of formula

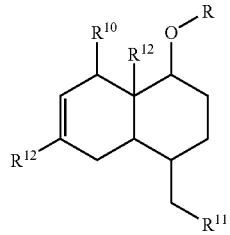

(III)

wherein R represents a hydrogen atom or a MeCO group;
$R^{10}$ and $R^{11}$ represent, each, a hydrogen atom or a methyl group;
one $R^{12}$ is a hydrogen atom and the other is a methyl group; and
the substituents $R^{10}$, $R^{11}$ and $R^{12}$ have in total 2 or 3 carbon atoms; in the form of any one of its stereoisomers or of a mixture thereof.

4. A perfuming composition according to claim 1, wherein the compound of formula (I) is selected from the group consisting of 4,6,8a-trimethyl-3,4,4a,5,8,8a-hexahydro-1(2H)-naphthalenone, 4,8,8a-trimethyl-1,2,3,4,4a,5,8,8a-octahydro-1-naphthalenyl acetate, perhydro-4-ethyl-8-methyl-1-naphthalenone, 4-ethyl-6,8-dimethyl-1,2,3,4,4a,5,8,8a-octahydro-1-naphthalenol, 2,6-dimethyltricyclo [6.2.1.0(2,7)]undec-9-en-3-ol, perhydro-4-ethyl-6,8a-dimethyl-1-naphthalenone, perhydro-8-methyl-4-propyl-1-naphthalenone and 4-ethyl-6,8a-dimethyl-3,4,4a,5,8,8a-hexahydro-1(2H)-naphthalenone.

5. A perfuming composition according to claim 4, wherein the compound of formula (I) is selected from the group consisting of 4,6,8a-trimethyl-3,4,4a,5,8,8a-hexahydro-1(2H)-naphthalenone, 4-ethyl-6,8-dimethyl-1,2,3,4,4a,5,8,8a-octahydro-1-naphthalenol, perhydro-8-methyl-4-propyl-1-naphthalenone and perhydro-4-ethyl-8-methyl-1-naphthalenone.

6. A compound of formula

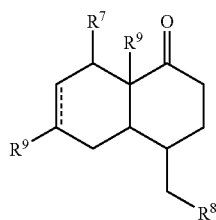
(II)

wherein the dotted lines represent a single or double bond;
$R^7$ and $R^8$ represent, each, a hydrogen atom or a methyl group;
$R^9$ are both hydrogen atoms or are both methyl groups; and
the substituents $R^7$, $R^8$ and $R^9$ have in total 2 or 3 carbon atoms; in the form of any one of its stereoisomers or of a mixture thereof;
or a compounds of formula

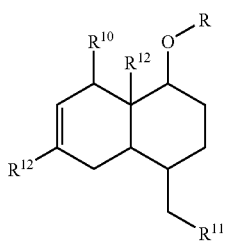
(III)

wherein R represents a hydrogen atom or a MeCO group;
$R^{10}$ and $R^{11}$ represent, each, a hydrogen atom or a methyl group;
one $R^{12}$ is a hydrogen atom and the other is a methyl group; and
the substituents $R^{10}$, $R^{11}$ and $R^{12}$ have in total 2 or 3 carbon atoms; in the form of any one of its stereoisomers or of a mixture thereof;
provided that 4,6,8,8a-tetramethyl-3,4,4a,5,8,8a-hexahydro-naphthalenone and 4,6,8a-trimethyl-3,4,4a,5,8,8a-hexahydro-1(2H)-naphthalenone and their isomers are excluded.

7. As a compound according to claim 6, 4-ethyl-6,8-dimethyl-1,2,3,4,4a,5,8,8a-octahydro-1-naphthalenol, perhydro-8-methyl-4-propyl-1-naphthalenone and perhydro-4-ethyl-8-methyl-1-naphthalenone.

8. A perfumed article comprising:
i) at least one compound of formula

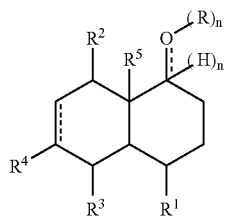
(I)

wherein the dotted lines represent a single or double bond and at least one of said dotted lines represents a double bond;
n represents simultaneously 0, in which case the oxygen atom is bounded to the cyclanic carbon atom by a double bond, or 1, in which case the oxygen atom is bounded to the cyclanic carbon atom by a single bond,
R represents a hydrogen atom or a HCO or MeCO group;
$R^1$ represents a linear or branched $C_1$-$C_4$ alkyl or alkenyl group;
$R^2$ represents a hydrogen atom or a methyl or ethyl group;
$R^3$ represents, taken alone, a hydrogen atom or, taken together with $R^2$, a bridging $CH_2$ group;
$R^4$ represents a hydrogen atom or a methyl or ethyl group; and
$R^5$ represents a hydrogen atom or a linear or branched $C_1$-$C_3$ alkyl group;
in the form of any one of its stereoisomers or of a mixture thereof; and
ii) a consumer product base.

9. A perfumed article according to claim 8, in the form of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

10. A perfumed article according to claim 8, wherein the compound of formula (I) is selected from the group consisting of 4,6,8a-trimethyl-3,4,4a,5,8,8a-hexahydro-1(2H)-naphthalenone, 4-ethyl-6,8-dimethyl-1,2,3,4,4a,5,8,8a-octahydro-1-naphthalenol, perhydro-8-methyl-4-propyl-1-naphthalenone and perhydro-4-ethyl-8-methyl-1-naphthalenone.

11. A method to confer, improve, enhance or modify the odor properties of a perfuming composition or a perfumed product, which method comprises adding to said composition or product an odour effective amount of at least a compound of formula

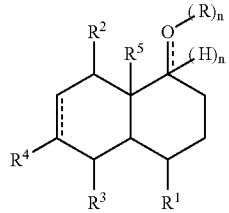
(I)

wherein the dotted lines represent a single or double bond and at least one of said dotted lines represents a double bond;
n represents simultaneously 0, in which case the oxygen atom is bounded to the cyclanic carbon atom by a double bond, or 1, in which case the oxygen atom is bounded to the cyclanic carbon atom by a single bond,
R represents a hydrogen atom or a HCO or MeCO group;
$R^1$ represents a linear or branched $C_1$-$C_4$ alkyl or alkenyl group;
$R^2$ represents a hydrogen atom or a methyl or ethyl group;
$R^3$ represents, taken alone, a hydrogen atom or, taken together with $R^2$, a bridging $CH_2$ group;
$R^4$ represents a hydrogen atom or a methyl or ethyl group; and
$R^5$ represents a hydrogen atom or a linear or branched $C_1$-$C_3$ alkyl group;
in the form of any one of its stereoisomers or of a mixture thereof.

* * * * *